(12) United States Patent
Uber, III et al.

(10) Patent No.: US 9,707,342 B2
(45) Date of Patent: Jul. 18, 2017

(54) SHIELD ADAPTED TO FIT MEDICAL INJECTOR SYRINGE

(71) Applicant: BAYER MEDICAL CARE INC., Indianola, PA (US)

(72) Inventors: Arthur E. Uber, III, Pittsburgh, PA (US); Barry L. Tucker, Verona, PA (US); Mark Trocki, Cheswick, PA (US); Raymond C. Hoffman, Gibsonia, PA (US); Marc A. Mabie, Pittsburgh, PA (US)

(73) Assignee: BAYER HEALTHCARE, Whippany, NJ (US)

( * ) Notice: Subject to any disclaimer, the term of this patent is extended or adjusted under 35 U.S.C. 154(b) by 30 days.

(21) Appl. No.: 14/844,355

(22) Filed: Sep. 3, 2015

(65) Prior Publication Data

US 2015/0374914 A1  Dec. 31, 2015

Related U.S. Application Data (63) Continuation of application No. 13/831,769, filed on Mar. 15, 2013, now Pat. No. 9,125,976.
(Continued)

(51) Int. Cl.
| | |
|---|---|
| *A61N 5/00* | (2006.01) |
| *A61M 5/178* | (2006.01) |
| *G21F 5/018* | (2006.01) |
| *G21F 5/06* | (2006.01) |
| *A61M 5/00* | (2006.01) |

(Continued)

(52) U.S. Cl.
CPC .......... *A61M 5/1785* (2013.01); *A61M 5/007* (2013.01); *A61M 5/31* (2013.01); *A61N 5/1002* (2013.01); *A61N 5/1007* (2013.01); *G21F 5/018* (2013.01); *G21F 5/06* (2013.01); *A61M 2005/3104* (2013.01); *A61M 2205/0211* (2013.01); *A61M 2205/0238* (2013.01); *A61N 2005/1021* (2013.01); *A61N 2005/1094* (2013.01)

(58) Field of Classification Search
CPC ......... A61N 2005/1094; A61N 5/1007; A61M 5/1785; G21F 5/00; G21F 5/06; G21F 5/015; G21F 5/018
USPC ................. 600/1–8; 250/506.1, 507.1, 515.1
See application file for complete search history.

(56) References Cited

U.S. PATENT DOCUMENTS

| | | |
|---|---|---|
| 2,019,402 A | 10/1935 | Duffy |
| 2,201,108 A | 5/1940 | Mahler et al. |

(Continued)

FOREIGN PATENT DOCUMENTS

| | | |
|---|---|---|
| DE | 4438361 C1 | 2/1996 |
| EP | 0309426 A2 | 3/1989 |

(Continued)

OTHER PUBLICATIONS

Counterpart Partial European Search Report EP10015627, Mar. 23, 2011.

(Continued)

*Primary Examiner* — John Lacyk
(74) *Attorney, Agent, or Firm* — David Schramm; Joseph L. Kent; James R. Stevenson (57) ABSTRACT

A syringe shield useful for containing a syringe loaded with radioactive and/or light sensitive drugs is disclosed. The syringe shield may reduce a healthcare provider's exposure to radiation and/or may reduce or eliminate ambient light contamination to optically sensitive components in the syringe.

20 Claims, 8 Drawing Sheets

Related U.S. Application Data (60) Provisional application No. 61/665,484, filed on Jun. 28, 2012, provisional application No. 61/656,743, filed on Jun. 7, 2012.

(51) Int. Cl.
*A61N 5/10* (2006.01)
*A61M 5/31* (2006.01)

(56) References Cited

U.S. PATENT DOCUMENTS

| | | |
|---|---|---|
| 2,725,058 A | 11/1955 | Rathkey |
| 2,761,717 A | 9/1956 | Mahlke |
| 3,064,648 A | 11/1962 | Bujan |
| 3,193,615 A | 7/1965 | Burrows |
| 3,308,979 A | 3/1967 | Hailes |
| 3,470,929 A | 10/1969 | Stephen |
| 3,584,625 A | 6/1971 | Swick |
| 3,596,939 A | 8/1971 | Gibson |
| 3,718,138 A | 2/1973 | Alexandrov et al. |
| 3,790,804 A | 2/1974 | Hunt |
| 3,876,319 A | 4/1975 | Meyer |
| 3,973,554 A | 8/1976 | Tipton |
| 3,984,695 A | 10/1976 | Collica et al. |
| 4,092,546 A | 5/1978 | Larrabee |
| 4,161,178 A | 7/1979 | Genese |
| 4,307,713 A | 12/1981 | Galkin et al. |
| 4,342,337 A | 8/1982 | Underwood |
| 4,344,435 A | 8/1982 | Aubin |
| 4,372,336 A | 2/1983 | Cornell et al. |
| 4,401,108 A | 8/1983 | Galkin et al. |
| 4,409,966 A | 10/1983 | Lambrecht et al. |
| 4,472,403 A | 9/1984 | Trijzelaar et al. |
| 4,562,829 A | 1/1986 | Bergner |
| 4,585,009 A | 4/1986 | Barker et al. |
| 4,798,404 A | 1/1989 | Iyanicki |
| 4,834,708 A | 5/1989 | Pillari |
| 4,883,459 A | 11/1989 | Calderon |
| 4,902,282 A | 2/1990 | Bellotti et al. |
| 4,911,697 A | 3/1990 | Kerwin |
| 4,968,305 A | 11/1990 | Takahashi et al. |
| 4,969,176 A | 11/1990 | Marinus |
| 4,994,012 A | 2/1991 | Nakayama et al. |
| RE33,585 E | 5/1991 | Haber et al. |
| 5,105,844 A | 4/1992 | King, Sr. |
| 5,176,415 A | 1/1993 | Choksi |
| 5,274,239 A | 12/1993 | Lane et al. |
| 5,286,067 A | 2/1994 | Choksi |
| 5,312,377 A | 5/1994 | Dalton |
| 5,383,858 A | 1/1995 | Reilly et al. |
| 5,452,748 A | 9/1995 | Simmons et al. |
| 5,460,609 A | 10/1995 | O'Donnell |
| 5,472,403 A | 12/1995 | Cornacchia et al. |
| 5,490,680 A | 2/1996 | Patel et al. |
| 5,503,187 A | 4/1996 | Simmons et al. |
| 5,509,911 A | 4/1996 | Cottone, Sr. et al. |
| 5,514,071 A | 5/1996 | Sielaff, Jr. et al. |
| 5,515,851 A | 5/1996 | Goldstein |
| 5,520,653 A | 5/1996 | Reilly et al. |
| 5,559,324 A | 9/1996 | Rapkin et al. |
| 5,569,181 A | 10/1996 | Heilman et al. |
| 5,573,515 A | 11/1996 | Wilson et al. |
| 5,676,406 A | 10/1997 | Simmons et al. |
| 5,739,508 A | 4/1998 | Uber, III |
| 5,800,397 A | 9/1998 | Wilson et al. |
| 5,800,400 A | 9/1998 | Hogan |
| 5,806,519 A | 9/1998 | Evans, III et al. |
| 5,810,988 A | 9/1998 | Smith, Jr. et al. |
| 5,828,073 A | 10/1998 | Zhu et al. |
| 5,840,026 A | 11/1998 | Uber, III et al. |
| 5,865,805 A | 2/1999 | Ziemba |
| 5,906,402 A | 5/1999 | Simmons et al. |
| 5,916,165 A | 6/1999 | Duchon et al. |
| 5,918,443 A | 7/1999 | Phillips |
| 5,927,351 A | 7/1999 | Zhu et al. |
| 5,947,890 A | 9/1999 | Spencer et al. |
| 6,001,083 A | 12/1999 | Wilner |
| 6,096,011 A | 8/2000 | Trombley, III et al. |
| 6,162,198 A | 12/2000 | Coffey et al. |
| 6,267,717 B1 | 7/2001 | Stoll et al. |
| 6,283,182 B1 | 9/2001 | Fedeli |
| 6,317,623 B1 | 11/2001 | Griffiths et al. |
| 6,397,098 B1 | 5/2002 | Uber, III et al. |
| 6,425,174 B1 | 7/2002 | Reich |
| 6,440,107 B1 | 8/2002 | Trombley, III et al. |
| 6,450,936 B1 | 9/2002 | Smith, III et al. |
| 6,453,188 B1 | 9/2002 | Ardenkjaer-Larsen et al. |
| 6,471,674 B1 | 10/2002 | Emig et al. |
| 6,520,930 B2 | 2/2003 | Critchlow et al. |
| 6,522,144 B2 | 2/2003 | Boskamp |
| 6,585,684 B1 | 7/2003 | Hughett et al. |
| 6,586,758 B2 | 7/2003 | Martin |
| 6,589,158 B2 | 7/2003 | Winkler |
| 6,614,040 B1 | 9/2003 | Zens |
| 6,672,244 B1 | 1/2004 | Martin |
| 6,761,725 B1 | 7/2004 | Grayzel et al. |
| 6,767,319 B2 | 7/2004 | Reilly et al. |
| 6,773,373 B2 | 8/2004 | Henneken et al. |
| 6,773,673 B1 | 8/2004 | Layfield et al. |
| 6,939,302 B2 | 9/2005 | Griffiths et al. |
| 7,018,363 B2 | 3/2006 | Cowan et al. |
| 7,040,856 B2 | 5/2006 | Reich |
| 7,086,133 B2 | 8/2006 | Reich |
| 7,105,846 B2 | 9/2006 | Eguchi |
| 7,151,267 B2 | 12/2006 | Lemer |
| 7,204,797 B2 | 4/2007 | Reilly et al. |
| 7,326,186 B2 | 2/2008 | Trombley et al. |
| 7,351,227 B2 | 4/2008 | Lemer |
| 7,419,478 B1 | 9/2008 | Reilly et al. |
| 7,457,804 B2 | 11/2008 | Uber et al. |
| 7,537,560 B2 | 5/2009 | Powers et al. |
| 7,563,249 B2 | 7/2009 | Schriver et al. |
| 7,611,486 B2 | 11/2009 | Jones et al. |
| 7,611,503 B2 | 11/2009 | Spohn et al. |
| 7,694,610 B2 | 4/2010 | Flores et al. |
| 7,731,106 B2 | 6/2010 | Doner et al. |
| 7,772,565 B2 | 8/2010 | Wilson |
| 7,905,861 B2 | 3/2011 | Rhinehart et al. |
| 7,935,141 B2 | 5/2011 | Randall et al. |
| 7,975,733 B2 | 7/2011 | Horppu et al. |
| 8,147,364 B2 | 4/2012 | Shioiri et al. |
| 8,192,397 B2 | 6/2012 | Griffiths et al. |
| 8,198,599 B2 | 6/2012 | Bouton et al. |
| 8,430,840 B2 | 4/2013 | Nazarifar et al. |
| 8,454,561 B2 | 6/2013 | Uber, III et al. |
| 8,540,698 B2 | 9/2013 | Spohn et al. |
| 8,551,074 B2 | 10/2013 | Hoffman et al. |
| 2002/0012593 A1 | 1/2002 | Okuda |
| 2002/0014429 A1 | 2/2002 | Johnson |
| 2003/0040700 A1 | 2/2003 | Hickle et al. |
| 2003/0144647 A1 | 7/2003 | Miyahara |
| 2003/0151256 A1 | 8/2003 | Guala |
| 2003/0153865 A1 | 8/2003 | Connell et al. |
| 2003/0222228 A1 | 12/2003 | Chen Fu et al. |
| 2004/0015038 A1 | 1/2004 | Lemer |
| 2004/0064041 A1 | 4/2004 | Lazzaro et al. |
| 2004/0068248 A1 | 4/2004 | Mooney et al. |
| 2004/0115038 A1 | 6/2004 | Nuesser et al. |
| 2004/0210199 A1 | 10/2004 | Atterbury et al. |
| 2004/0254525 A1 | 12/2004 | Uber et al. |
| 2004/0254533 A1 | 12/2004 | Schriver et al. |
| 2004/0260143 A1 | 12/2004 | Reilly et al. |
| 2005/0085682 A1 | 4/2005 | Sasaki et al. |
| 2005/0107698 A1 | 5/2005 | Powers et al. |
| 2005/0113754 A1 | 5/2005 | Cowan et al. |
| 2005/0171487 A1 | 8/2005 | Haury et al. |
| 2005/0203329 A1 | 9/2005 | Muto et al. |
| 2005/0203330 A1 | 9/2005 | Muto et al. |
| 2005/0230575 A1 | 10/2005 | Zelenski et al. |
| 2005/0234424 A1 | 10/2005 | Besing et al. |
| 2005/0234428 A1 | 10/2005 | Spohn et al. |
| 2005/0247893 A1 | 11/2005 | Fu et al. |
| 2005/0251096 A1 | 11/2005 | Armstrong et al. |
| 2005/0277833 A1 | 12/2005 | Williams, Jr. |

(56) References Cited

U.S. PATENT DOCUMENTS

| | | |
|---|---|---|
| 2006/0051531 A1 | 3/2006 | Kashiwamura |
| 2006/0086909 A1 | 4/2006 | Schaber |
| 2006/0151048 A1 | 7/2006 | Tochon-Danguy et al. |
| 2006/0293553 A1 | 12/2006 | Polsinelli et al. |
| 2007/0034537 A1 | 2/2007 | Fago et al. |
| 2007/0066937 A1 | 3/2007 | Jones et al. |
| 2007/0088262 A1 | 4/2007 | Jones et al. |
| 2007/0088272 A1 | 4/2007 | Jones et al. |
| 2007/0123829 A1 | 5/2007 | Atterbury et al. |
| 2007/0129591 A1 | 6/2007 | Yanke et al. |
| 2007/0129705 A1 | 6/2007 | Trombley, III et al. |
| 2007/0161970 A1 | 7/2007 | Spohn et al. |
| 2008/0038839 A1 | 2/2008 | Linder et al. |
| 2008/0131362 A1 | 6/2008 | Rousso et al. |
| 2008/0177126 A1 | 7/2008 | Tate et al. |
| 2008/0200747 A1 | 8/2008 | Wagner et al. |
| 2008/0242915 A1 | 10/2008 | Jackson et al. |
| 2009/0131862 A1 | 5/2009 | Buck et al. |
| 2010/0063481 A1 | 3/2010 | Hoffman et al. |
| 2010/0160889 A1 | 6/2010 | Smith et al. |
| 2010/0185040 A1 | 7/2010 | Uber, III et al. |
| 2011/0021905 A1 | 1/2011 | Patrick et al. |
| 2011/0132482 A1 | 6/2011 | Honma et al. |
| 2011/0178359 A1 | 7/2011 | Hirschman et al. |
| 2011/0201867 A1 | 8/2011 | Wagner |
| 2011/0208129 A1 | 8/2011 | Bonnette et al. |
| 2011/0209764 A1 | 9/2011 | Uber et al. |
| 2011/0214781 A1 | 9/2011 | Horppu et al. |
| 2012/0013121 A1 | 1/2012 | Weckstrom |
| 2013/0331801 A1 | 12/2013 | Hoffman et al. |

FOREIGN PATENT DOCUMENTS

| | | |
|---|---|---|
| EP | 0333276 A1 | 9/1989 |
| EP | 0349745 A1 | 1/1990 |
| EP | 0915760 B1 | 5/2002 |
| EP | 1616587 A1 | 1/2006 |
| EP | 1927996 A2 | 6/2008 |
| GB | 429365 A | 5/1935 |
| GB | 2040379 A | 8/1980 |
| GB | 2299162 A | 9/1996 |
| IT | RM96A000148 | 3/1996 |
| JP | S5184686 A | 7/1976 |
| JP | 360236079 A | 11/1985 |
| JP | H05272685 A | 10/1993 |
| JP | H06165820 A | 6/1994 |
| JP | 2000350783 A | 12/2000 |
| JP | 2002341040 A | 11/2002 |
| JP | 2003176892 A | 6/2003 |
| JP | 2004290455 A | 10/2004 |
| JP | 2005024291 A | 1/2005 |
| JP | 2005283431 A | 10/2005 |
| JP | 2008515603 A | 5/2008 |
| WO | 0137904 A2 | 5/2001 |
| WO | 2004004787 A2 | 1/2004 |
| WO | 2005049110 A2 | 6/2005 |
| WO | 2006044409 A2 | 4/2006 |
| WO | 2006051531 A2 | 5/2006 |
| WO | 2006124775 A2 | 11/2006 |
| WO | 2007010534 A2 | 1/2007 |
| WO | 2008011401 A2 | 1/2008 |
| WO | 2008076150 | 6/2008 |
| WO | 2008083313 A2 | 7/2008 |
| WO | 2009014367 A2 | 1/2009 |
| WO | 2009/107930 | 9/2009 |
| WO | 2009/142944 | 11/2009 |
| WO | 2009149367 A1 | 12/2009 |

OTHER PUBLICATIONS

European Search Report for European Application No. EP10015627, mailed on Jun. 16, 2011.

Feichtinger, M., et al., "Automatic and remote controlled ictal SPECT injection for seizure focus localization by use of a commmercial contrast agent application pump," Epilepsia, vol. 48, Issue 7, pp. 1409-1413 (Jul. 2007).

International Search Report from counterpart PCT Application No. PCT/US2009/046437 dated Aug. 11, 2009.

Lee, J. J., et al., "Ictal SPECT using an Attachable Automated Injector: Clinical Usefulness in the Prediction of Ictal Onset Zone," Acta Radiological, vol. 50, Issue 10, pp. 1160-1168 (Dec. 2009).

The Extended European Search Report dated Jun. 11, 2014 from corresponding EP Application No. EP09759525.

"Supplementary European Search Report dated Jan. 19, 2016 from EP13809067".

International Preliminary Report on Patentability and Written Opinion and International Search Report mailed May 21, 2015 from corresponding PCT Application No. PCT/US2013/044038.

International Search Report and Written Opinion mailed on May 21, 2014 from corresponding PCT Application No. PCT/US2014/017949 filed on Feb. 24, 2014.

BPL Series Brouchure, Value Plastics, Inc. www.valueplastics.com.

International Preliminary Report on Patentability for Application No. PCT/US2013/044021, mailed on Jun. 6, 2014, 9 pages.

International Search Report and Written Opinion for Application No. PCT/US2013/044021, mailed on Nov. 5, 2013, 10 pages.

SBL Series Quick Connects, Values Plastics, Inc. www.valueplastics.com.

International Preliminary Report on Patentability for Application No. PCT/US2013/048484, mailed on Dec. 31, 2014, 6 pages.

International Search Report and Written Opinion for Application No. PCT/US2013/048484, mailed on Oct. 22, 2013, 8 pages.

Supplementary European Search Report from EP Application No. EP13799972 dated Dec. 21, 2015.

SHIELD ADAPTED TO FIT MEDICAL INJECTOR SYRINGE

CROSS-REFERENCE TO RELATED APPLICATIONS

This application is a continuation application of U.S. Ser. No. 13/831,769, filed Mar. 15, 2013, now U.S. Pat. No. 9,125,976, which claims priority from U.S. Provisional No. 61/665,484 entitled "Radiation Shield Adapted to Fit a Medical MR Injector Syringe" filed Jun. 28, 2012, and U.S. Provisional No. 61/656,743 entitled "Radiopharmaceutical Delivery and Tube Management System", filed Jun. 7, 2012, each of which is incorporated by reference herein in its entirety.

BACKGROUND

Administration of radioactive pharmaceutical substances or drugs, generally termed radiopharmaceuticals, is often used in the medical field to provide information or imagery of internal body structures and/or functions including, but not limited to, bone, vasculature, organs and organ systems, and other tissue or as therapeutic agents to kill or inhibit the growth of targeted cells or tissue, such as cancer cells. Radiopharmaceutical agents used in imaging procedures and therapeutic procedures typically include highly radioactive nuclides of short half-lives and are hazardous to attending medical personnel. These agents are toxic and can have physical and/or chemical effects for attending medical personnel such as clinicians, imaging technicians, nurses, and pharmacists. Excessive radiation exposure is harmful to attending medical personnel due to their occupational repeated exposure to the radiopharmaceuticals. The constant and repeated exposure of medical personnel and patients to radiopharmaceuticals over an extended period of time is a significant problem in the nuclear medicine field.

Administration of optically sensitive substances is an additional concern in the medical field. These substances are often used for imaging purposes and if exposed to ambient light contamination can have reduced function or complete loss of function. It is a significant problem if these substances become contaminated from ambient light and it is of high importance to have these substances protected from exposure to ambient light in order to preserve their function before delivery to the patient.

BRIEF SUMMARY

Various embodiments are directed to syringe shields including a first shield panel having a syringe bore designed and configured to correspond to the shape of a syringe and a second shield panel having a syringe bore designed and configured to correspond to the shape of a syringe wherein reversible coupling of the first shield panel and the second shield panel provides a syringe bore configured to encase a syringe and provide a plunger access bore configured to allow access to a plunger associated with the syringe. In some embodiments, the first shield panel and the second shield panel may be hingedly attached.

In such embodiments, the first shield panel and the second shield panel may include or be composed of a radioactive emissions blocking material, and in certain embodiments, a syringe may be completely or nearly completely encased by the radioactive emissions blocking material when the first shield panel and the second shield panel are coupled. The radiation emissions blocking material is not limited and can include, but are not limited to, materials such as tungsten, tungsten alloys, molybdenum, molybdenum allows, lead, lead alloys, lead-lined wood, leaded glass, polymer composite materials, ceramic materials, borated polymers, and combinations thereof. In other embodiments, the first shield panel and the second shield panel may include or be composed of an optical blocking material, and in certain embodiments, a syringe may be completely or nearly completely encased by the optical blocking material when the first shield and the second shield panel are coupled. The optical blocking material is not limited and can include, but are not limited to, materials such as metals, metal alloys, wood, dark colored glass, non-clear polymer composite materials, ceramic materials, or any other material that may block ambient light contamination.

In some embodiments, the syringe bore may be sized to accommodate a syringe having a diameter sufficient to hold 0.5 ml, 1 ml, 3 ml, 5 ml 10 ml, 15 ml, 20 ml, 30 ml, 40 ml, 50 ml, 60 ml, and combinations thereof. In particular embodiments, the syringe shield may include an integrated cap, and in other embodiments, the syringe shield may include a removable cap. In some embodiments, the syringe shield may include a sleeve encasing the first shield panel, the second shield panel, or combinations thereof. In various embodiments, the sleeve is composed of a material selected from the group consisting of metals, metal alloys, polymeric materials, polymer composites material, and combinations thereof, and in certain embodiments, the sleeve may be composed of aluminum or polycarbonate. In particular embodiments, the sleeve may be integrally attached to each of the first shield panel and the second shield panel, and such sleeves may be composed of, for example, metals, metal alloys, polymeric materials, polymer composite materials, and combinations thereof or, in particular embodiments, aluminum or polycarbonate.

In some embodiments, the syringe shield may include a clamping means configured to connect the first shield panel and the second shield panel. In particular embodiments, each of the first shield panel and the second shield panel may include hinge extensions and the syringe shield further comprises a hinge pin received by the hinge extensions, and in some embodiments, each of the first shield panel and the second shield panel may include one or more connector plates. In some embodiments, the syringe shield may include a collar configured and arranged to reversibly connect to the first shield panel and the second shield panel and connect the syringe shield to a device or base plate. In some embodiments, the syringe shield may include a carrier handle, and in certain embodiments, the carrier handle may be configured to be reversibly attached to the first and second shield panels.

BRIEF DESCRIPTION OF DRAWINGS

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

DETAILED DESCRIPTION

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

For purposes of the description hereinafter, the terms "upper," "lower," "right," "left," "vertical," "horizontal," "top," "bottom," "lateral," "longitudinal," and derivatives thereof shall relate to the orientation of embodiments disclosed in the drawing figures. However, it is to be understood that embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

It is to be understood that the disclosed embodiments may assume various alternative variations and step sequences, except where expressly specified to the contrary. It is also to be understood that the specific devices and processes illustrated in the attached drawings, and described in the following specification, are simply exemplary embodiments.

Various embodiments are directed to a syringe shield that is configured to reduce or eliminate exposure of the operator, subject, or other injected organism to radioactive emissions from a radiopharmaceutical in a syringe and to reduce or eliminate ambient light contamination to optical components in a syringe. In other embodiments, shielding components may stabilize radiopharmaceuticals or optical tracers thermally and mechanically. For example, shielding components may be designed to reduce or eliminate exposure of an optical tracer to light which can quench fluorescence and cause the tracer to become heated or chemically modified over time reducing the optical output or chemical or enzymatic activity of the tracer.

In various embodiments, the syringe shield may include one or more shield panels, and in some embodiments the one or more shield panels may be encased by one or more interconnected sleeves to form the syringe shield. In some embodiments, the shield panels and sleeves may be integrated together such that each sleeve contains a shield panel that is fixedly attached to the sleeve. In other embodiments, the shield panels and sleeves may be separate parts that are designed to be combined around the syringe to create the syringe shield. For example, in some embodiments, two or more shield panels may be placed over a syringe and a hinged sleeve may be placed around the two or more shield panels and locked into place over the syringe. The shield may have any number of shield panels and sleeve components. For example, in some embodiments, the syringe shield may have 1, 2, 3, 4, 5, or 6 shield panels and 1, 2, 3, 4, 5, or 6 sleeve components to encase the shield panels.

In some embodiments, the shield panels contain radioactive emissions blocking material such as, for example, tungsten, tungsten alloys, molybdenum, molybdenum allows, lead, lead alloys, lead-lined wood, leaded glass, polymer composite materials, ceramic materials, borated polymers, and the like and combinations thereof. In certain embodiments, the one or more shield panels may be tungsten. In some embodiments, the sleeves encasing the panels may be composed of any material including metals, metal alloys, polymeric materials, polymer composite materials, and the like and combinations thereof. In particular embodiments, the sleeves may be aluminum or polycarbonate. In further embodiments, the sleeves and shield panels may be integrated together. The syringe shield may contain little or no magnetic materials and little or no electronics.

Figure 1:
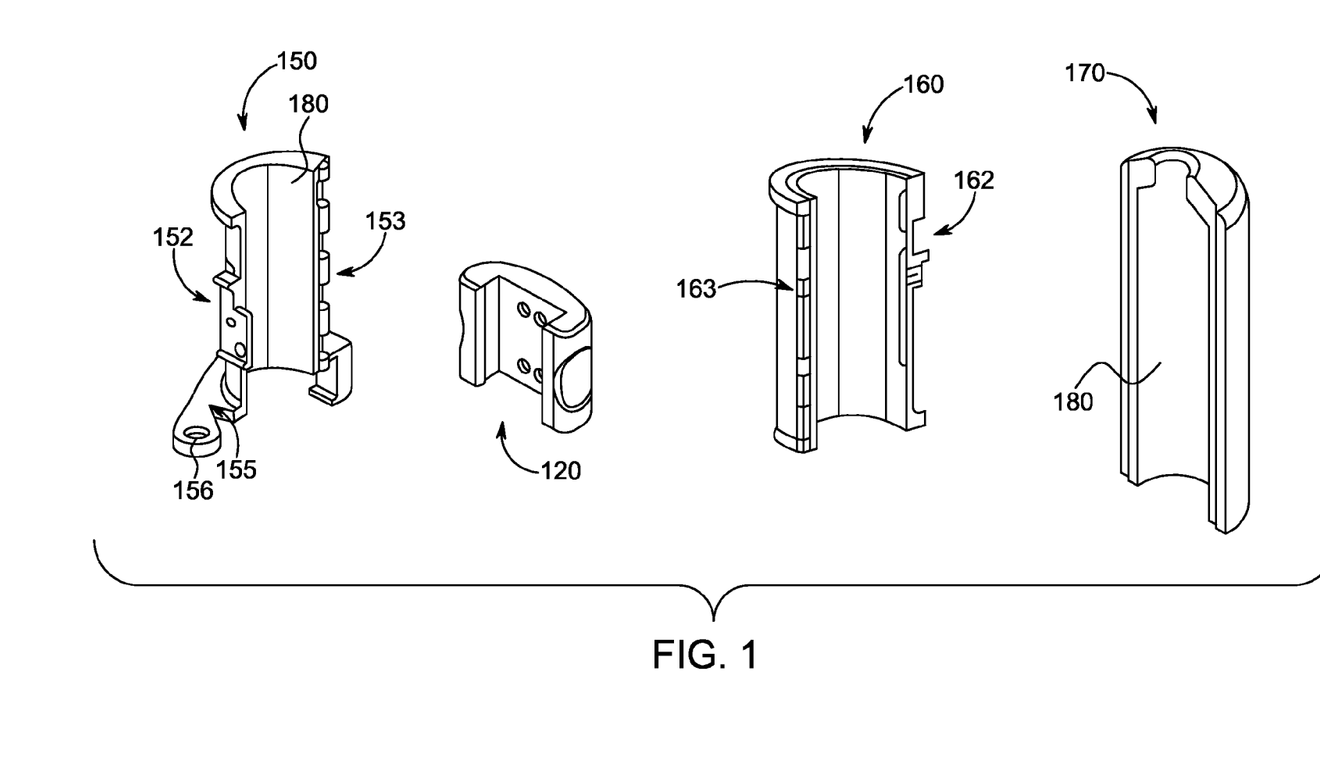
FIG. 1 is a drawing showing a syringe sleeve with and without a pivot and a sleeve cover.
Figure 6:
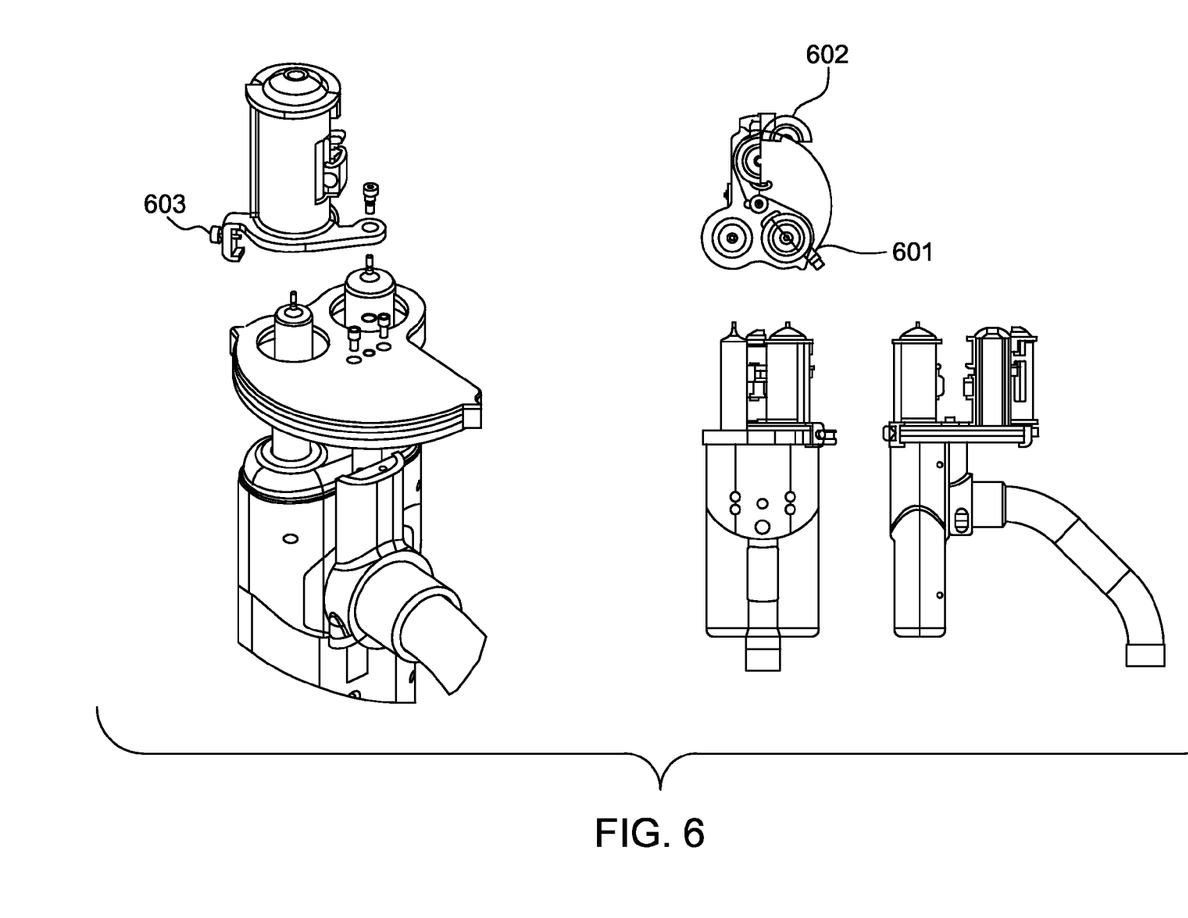
FIG. 6 is a drawing showing a shield and support structure mounted on an injector system.

FIG. 1 is an example of a syringe shield having two shield panels 150, 160. Each shield panel 150, 160 includes a syringe bore 180 designed and configured to correspond to the shape of a syringe. The syringe bore 180 may be configured to accommodate any syringe or type of syringe known in the art, and in some embodiments, the syringe bore may provide a universal fitting for syringes of various types and sizes. For example, the syringe shield may be intentionally larger than the syringes that will likely be used with the syringe shield. In other embodiments, the size of the syringe bore 180 may closely match the size of the syringe to be used with the syringe shield. For example, in particular embodiments, the syringe bore may be configured to accommodate syringes having similar flange sizes and body lengths but different body diameters. Therefore, a syringe having a diameter sufficient to allow the syringe to hold 10 ml, 15 ml, 20 ml, 30 ml, 40 ml, 50 ml, 60 ml, or 65 ml and a syringe having a diameter sufficient to allow the syringe to hold 1 ml, 3 ml, 5 ml or 10 ml can be securely held within the syringe bore. Alternatively, shield panel 170 may be inserted into bore 180 to provide the shielding material that closely fits the selected syringe. In such embodiments, 150 and 160 act as sleeves. An element 170 is placed (generally but not necessarily permanently) into each of 150 and 160 to act as the shield panel. FIG. 6 shows the assembled unit.

In some embodiments, the syringe shield may be tapered on a forward end to accommodate the shape of the tapered end of a common syringe, and in such embodiments, the syringe shield may include an additional smaller bore at the tapered end that may provide an access point to the syringe when the syringe is enclosed within the shield. In some embodiments, the forward end of the syringe shield may be domed such that the tapered end of the syringe is enclosed under the dome, but outer surfaces of the syringe do not physically contact the domed portion of the syringe shield. As with the tapered forward end, the domed forward end may include an additional bore to provide access to the syringe when the syringe is encased in the syringe shield.

The aft portion of the syringe shield may be designed to allow the syringe encased in the syringe shield to be accessed and contacted by a device for expelling the contents of the syringe such as a piston, rod, or plunger. In some embodiments, such as that depicted in FIG. 1, the aft portion of the syringe shield may be open and continuous with the bore. Thus, any means for expelling the syringe can easily reach the syringe. In other embodiments, the aft portion of the syringe shield may be partially enclosed. For example, in some embodiments, the aft portion of each shield panel 150, 160 may be enclosed with a center bore such that when the shield panels 150, 160 are combined a circular center bore is provided that allows access to a piston or plunger to contact the syringe. The size of the circular center bore may vary among embodiments and may be sufficiently sized to allow access to the syringe while blocking at least a portion of the radiation from the syringe or to block ambient light contamination to optical components in the syringe.

In some embodiments, the shield panels 150, 160 may be connected. For example, in some embodiments, the shield panels 150, 160 may be hingedly attached to one another to produce a clam shell syringe shield. In other embodiments, the shield panels 150, 160 may be individual devices that can be reversibly connected to one another during use. For example, as illustrated in FIG. 1, each shield panel 150, 160 may include one or more appendages 152, 162, one or more hinge extensions 153, 163, one or more connector plates 155, and the like or combinations thereof.

In embodiments, such as those shown in FIG. 1, the shield panels 150, 160 may contact one another such that the hinge extensions 153, 163 interconnect allowing a continuous bore to be created through the aligned hinge extensions 153, 163. A hinge pin (not shown) may be placed through the continuous bore facilitating a connection between the shield panels 150, 160. In some embodiments, the hinge pin may be permanently held within the continuous bore by, for example, providing a cap or flange on either end of the hinge pin after it has been placed in the continuous bore. In other embodiments, the hinge pin may be removable, and in certain embodiments, the hinge pin may include a handle to allow at least one end of the hinge pin to be easily grasped and manipulated.

The shield panels 150, 160 of the example shield illustrated in FIG. 1 further include appendages 152, 162 that align when the shield panels are brought into contact with one another. In some embodiments, one or both shield panels 150, 160 may include a clasp (not shown) or other closure device that is fixedly attached to one of the shield panels 150, 160, and is capable of contacting and holding an appendage 152, 162 of the other shield panel 150, 160 to effect a reversible connection. In other embodiments, an appendage 152 on one shield panel 150 may be aligned with an appendage 162 on another shield 160 and a clamping device 120 be used to hold the aligned appendages 152, 162 together facilitating a reversible connection. The clamping device 120 can be held in place using any means known in the art including, for example, a tension screw, a spring loaded ball detent, a hinge, various clamping mechanism, and the like or combinations thereof.

The shield panels 150, 160 may further include one or more connector plates 155. The connector plates 155 are, generally, a lateral extension or flange extending from one end of the shield panels. In some embodiments, the connector plate 155 may facilitate connection of the shield panels 150, 160, and in certain embodiments, the connector plate 155 may facilitate connection between the shield and a device. In some embodiments, the connector plate 155 may fit within a groove on a surface of the device that holds the shield in place on the device. In other embodiments, a magnet or other electromagnetic connection may be made between the device and the shield, and in still other embodiments, the connector plate 155 may include one or more orifices 156 through which a connector pin or screw may be passed that operably connects the shield to the device. Devices may be any devices that hold radiation or optically sensitive components or containers including radioactive or optically sensitive materials. In certain embodiments, the device may be a fluid delivery device or system, and in some embodiments, such fluid delivery devices or systems may be designed and configured to deliver radiopharmaceuticals or optically sensitive components.

The connector plate 155 may be separated from one another when the shield panels 150, 160 are connected to form the shield, for example, connector plates may be on opposing sides of the shield. In other embodiments, the connector plates may contact one another at joints along the circumference of the shield to produce a continuous flange around a circumference of the shield, and in still other embodiments, the connector plates 155 may be interconnected when the shield panels 150, 160 are aligned. For example, a first connector plate 155 may be configured to receive the second connector plate (not shown) when the shield panels are aligned such that orifices 156 on each connector plate 155 align to produce a continuous opening through which a connector pin, screw, or bolt can be passed. In such embodiments, the connector plate may provide both a reversible connection between shield panels 150, 160 and a reversible connection to a device. In some embodiments, only one shield panel 150 contains a connector plate 155, which may be used to connect the shield to a mounting support or device. The second shield plate 160 is connected to the first shield plate 150, for example, through hinges 163, 153 and through the connector plate 155 of shield panel 150 both panels 150, 160 are connected to a mounting support or device.

In some embodiments, an upper or forward portion of the syringe shield may be open as illustrated in FIG. 1. In other embodiments, the syringe shield may include an integrated cap that encloses around the forward end of the shield allowing for minimal emissions from the shielded syringe. In such embodiments, the cap may include a bore providing access to the nozzle of the syringe. In other embodiments, a removable cap may be attached to the shield after the shield panels are in connection with one another. The removable cap may be attached to the shield panels by any means, such as, for example a threaded assembly, a snap enclosure, a slide fit, a vacuum seal, and the like and combinations thereof. As in the integrated cap, the removable cap may include a bore to allow for tubing or other fluid path elements to the nozzle of the syringe. In some embodiments, the bore may include a shoulder to properly position the syringe within the forward portion of the syringe shield when being prepared for injection.

Figure 2:
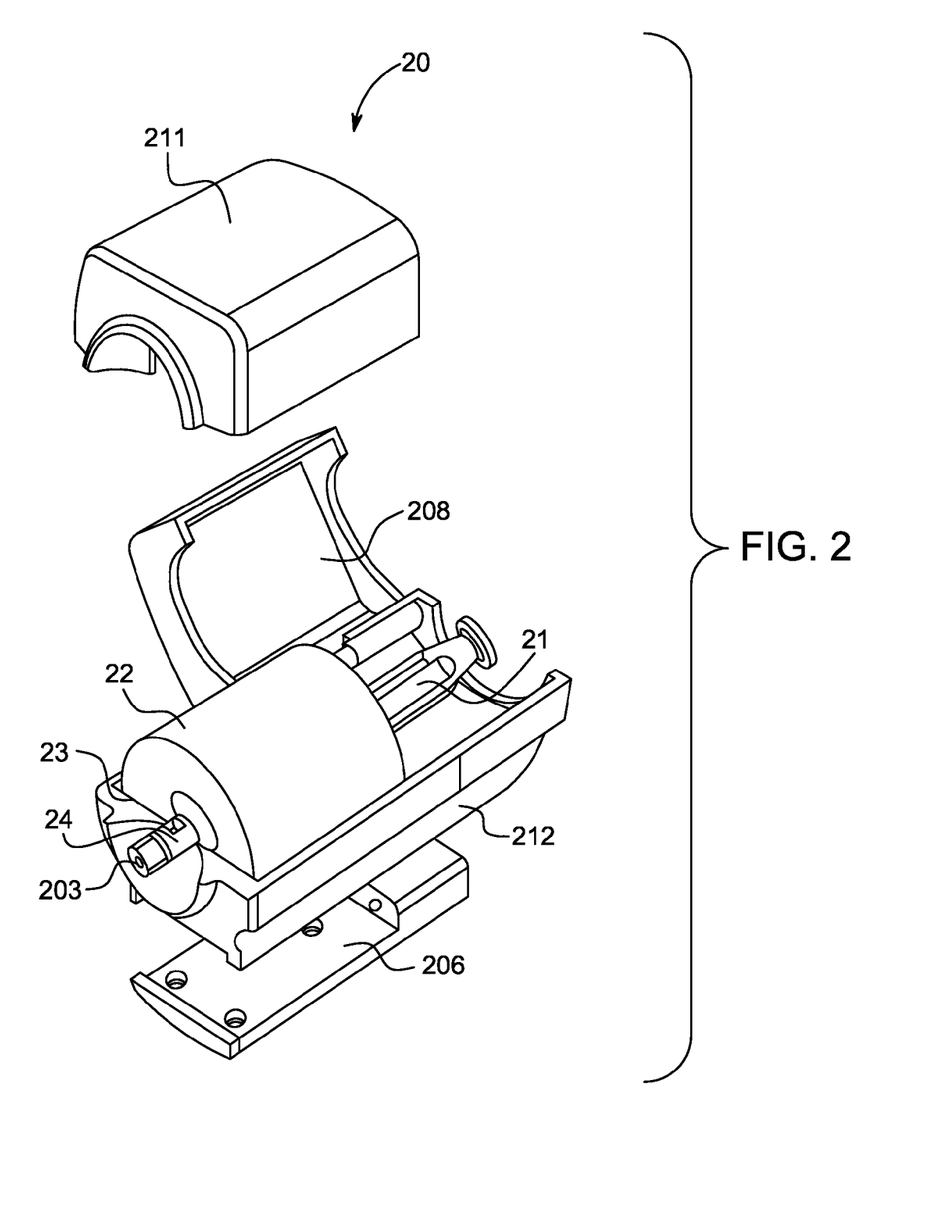
FIG. 2 is a drawing showing an embodiment of a syringe shield.

In particular embodiments, the syringe shield may include one or more sleeves that cover the shield panels to facilitate attachment of the shield panels and/or improve handling. For example, FIG. 2 shows another example of a syringe shield 20 having an upper housing sleeve 211 and a lower housing sleeve 212. In some embodiments, the upper housing sleeve 211 and the lower housing sleeve 212 may encase a shield panel 22 containing a bore (not shown) capable of housing a syringe 21. As illustrated in FIG. 2, the syringe shield 20 may include various addition housing or sleeve sections. For example, the syringe shield may include one or more removable or hinged segments 208 that encase, for example, a plunger portion of the syringe 21, a piston, a rod, or other means for expelling the contents of the syringe. In some embodiments, the upper housing sleeve 211 may be removeably attached to the lower housing sleeve 212 by any means including pressure fittings, snaps, screws, clamps, bolts, pins, and the like and combinations thereof, and in other embodiments, the upper housing sleeve 211 may be fixedly attached to the lower housing sleeve 212 by, for example, welding or gluing. In other embodiments, the upper housing sleeve 211 and the lower housing sleeve 212 may be connected by, for example, a hinge. In still other embodiments, the upper housing of the syringe shield 20 may include a hinged syringe access door 208 that allows access to part of the internal segments of the syringe shield 20. For example, as illustrated in FIG. 2 a hinged access door 208 may allow access to the syringe 21 such that the user can more easily maneuver the syringe while inserting it into the syringe shield 22. The upper housing sleeve 211 may be fixedly attached to the lower housing sleeve 212, for example, the upper housing sleeve 211 and lower housing sleeve 212 may be hingedly attached to each other in a clam shell configuration.

Figure 3A:
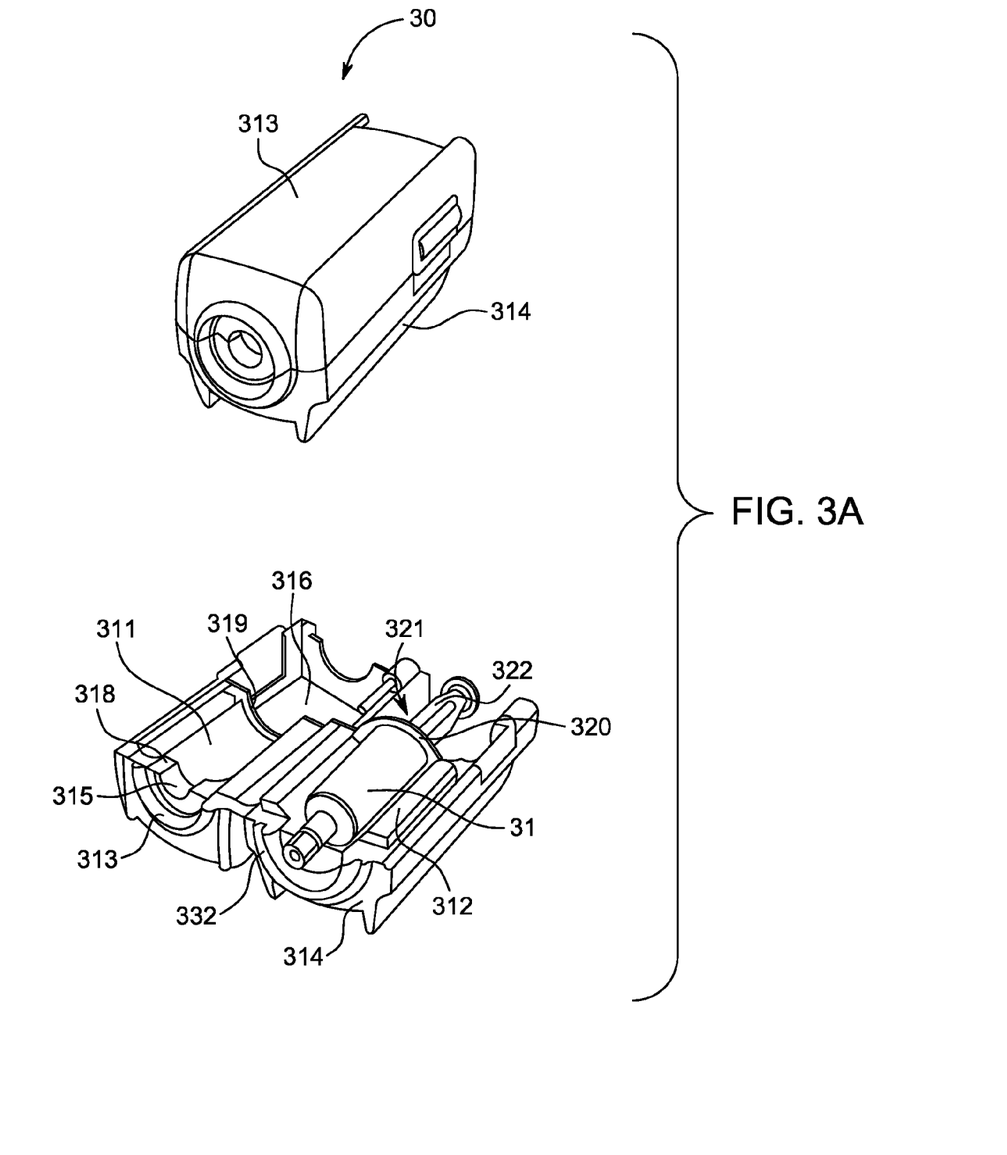
FIG. 3A is a drawing showing a second embodiment of a syringe shield having latched, clam shell syringe access.

In other embodiments, the syringe shield has shield panels which may be incorporated in the sleeves. As illustrated in FIG. 3A, in some embodiments, the syringe shield 30 may be designed to include a radioactive shield panel 311 in the upper housing sleeve 313 and a shield panel 312 in the lower housing sleeve 314. As illustrated in FIG. 3A, shield panels 311, 312 may be incorporated into the syringe housing such that the syringe 31 is completely or nearly completely encased by the radioactive emissions blocking material when the syringe shield sleeves are in the closed position, and the upper housing 313 or any part thereof can be hingedly attached to the lower housing 314 to allow access to the syringe 31. In some embodiments, the syringe bore 315 may be configured and designed to accommodate a syringe 31. Such a syringe bore may include a shoulder 318 positioned to contact a front portion of the syringe and syringe bore 315 to provide a means for accessing the outlet portion of the syringe.

An aft groove 319 associated with the plunger access bore 321 may also be provided to accommodate a flanged portion 320 of the syringe 31. In certain embodiments, the plunger 322 of the syringe or another actuation means may fit within an enlarged portion 316 of the shield 30 that allows user access to the syringe 31 and plunger 322. The enlarged portion of the housing may further accommodate the piston or other part of the actuation component that is configured to associate with the plunger 322 allowing the plunger to advance and retract. In some embodiments, the enlarged portion may include additional shield panels or extensions of the shield panels 311, 312. In other embodiments, the enlarged portion may not include additional shielding.

Figure 3B:
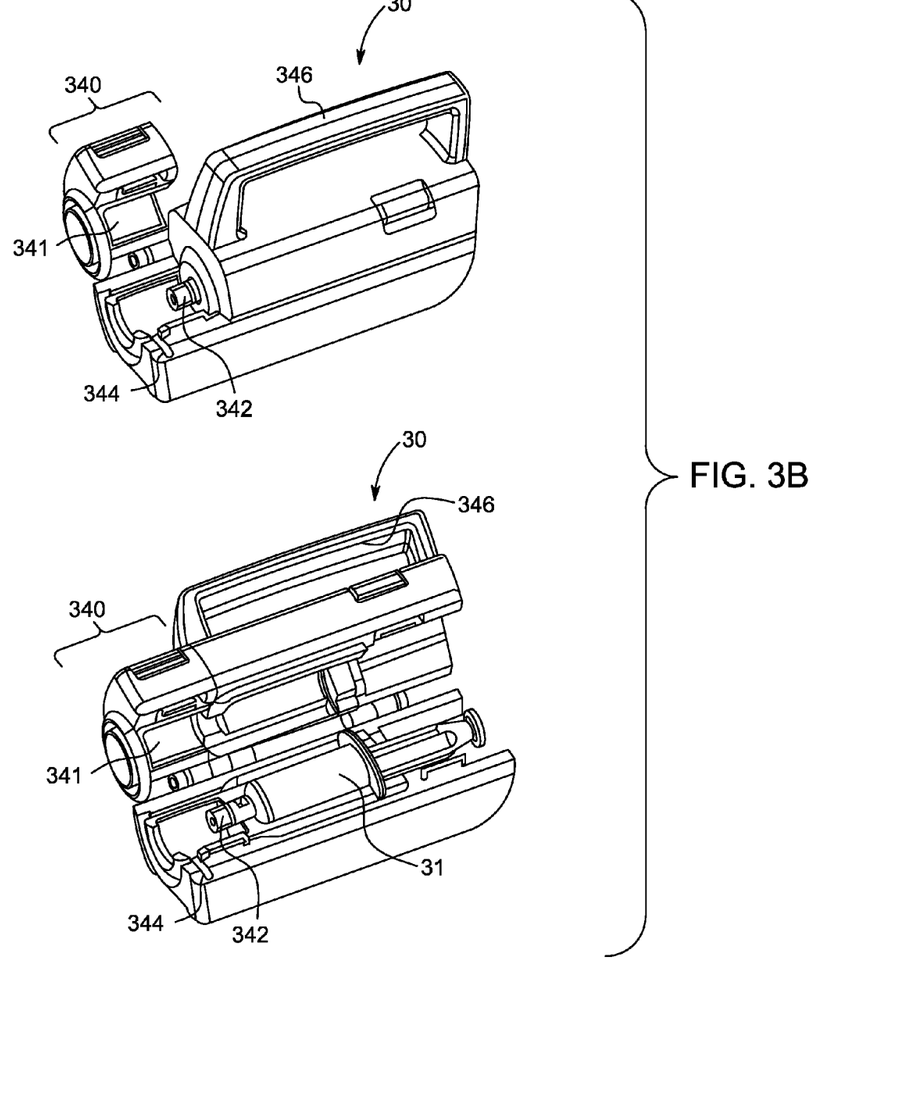
FIG. 3B is a drawing showing a syringe shield with a forward enlarged portion and a carrier handle

While FIG. 3A illustrates a syringe shield 30 having an aft enlarged portion, in certain embodiments, the syringe shield may include a forward enlarged portion 340, as illustrated in FIG. 3B, to encase tubing or other extensions from the syringe. In some embodiments, as illustrated in FIG. 3B the syringe shield may include a forward enlarged portion 340 with an access bore 341 designed to encase a connector portion 342 of the syringe 31 and a portion of the tubing extending from the connector 342 of the syringe 31 to a delivery device. In other embodiments, the forward enlarged portion 340 may include a lateral access bore provided on a side of the forward enlarged portion 340 while the forward section of the forward enlarged portion 340 remains enclosed and shielded. Without wishing to be bound by theory, a lateral bore may allow for a reduction in shine from the forward end of the syringe thereby reducing light exposure or potential irradiation of the user or to reduce or eliminate ambient light contamination to optically sensitive components in a syringe. The forward enlarged portion 340 may be connected to the syringe shield 30 and form part of the syringe shield 30. In some embodiments, the forward enlarged portion 340 may be separately attached to the syringe shield 30 and may include a separate hinged portion that allows access to the connector 342 and tubing section when the syringe 31 is encased in the syringe shield 30. In certain embodiments, the forward extension 341 may include a lateral exit port 344 through which the tubing section may exit the syringe shield 30. The forward section of the access bore 341 may be enclosed with a blocking material to reduce shine from the connector 342 and potential exposure of the user to radiation or to reduce or eliminate ambient light contamination to optically sensitive components in a syringe. FIG. 3B additionally shows a syringe shield 31 having a built in handle 346 which is further described below with FIG. 7.

In some embodiments, a connection between the shield and a device may be facilitated by a locking mechanism that is integrated into the housing. For example, as illustrated in FIG. 2, the syringe shield 20 of such embodiments may attach to a delivery injector body (not shown) using a syringe mount system which may include one or more flanges or grooves configured to associate with a syringe mount 206. The syringe mount 206 of such embodiments may be in any configuration and may include, for example, buttons, pins, slides, grooves, and the like configured to associate with the syringe shield 20 to facilitate proper placement of the housing on or within the delivery injector body. In other embodiments, the syringe shield 20 may attach to a delivery injector body through a saddle mount which may be shaped to fit within a groove provided on the syringe shield 20. In some embodiments, the saddle mount may include pressure fittings, grooves, pins, buttons, and the like that facilitate reversible attachment of the syringe shield 20 to the saddle mount. The saddle mount of such embodiments may be similar to a ski boot connector in which a first flange on the syringe shield 20 is inserted into a groove on the saddle mount and a second flange or groove is received by a hinged clamp that holds the second flange or groove in the mount. The hinged clamp may include one or more springs that are positioned to apply force to the second flange or groove holding it in place. The hinged clamp may be forced backward by a lateral flange on the syringe shield that contacts the hinged clamp when, for example, the syringe shield is pivoted in the saddle mount.

In various embodiments, the syringe mount may be associated with and attached to a framework underlying the housing rather than the housing itself. The framework will generally be composed of a rigid material that provides mechanical support for the syringe mount with a syringe shield mounted to the syringe mount and an actuation component mount. Without wishing to be bound by theory, the framework may substantially improve the accuracy and reproducibility of injections by reducing or eliminating flexion that can occur when the syringe mount and/or actuation component are attached to a housing composed of a more flexible material. In some embodiments, the framework may be composed of steel, aluminum, or another metal or metal alloy or high tensile strength polymer compositions and may be designed to fit within the housing and provide attachment sites for mechanical components of the device in addition to the syringe mount and actuation component.

In certain embodiments, the syringe mount may include a forward groove or ridge into which a corresponding ridge or groove on the syringe shield fits. The syringe mount may further include a rear binding that associates with a groove or ridge on the syringe shield. In some embodiments, the binding may include a housing attached to a delivery injector body that includes one or more springs positioned to urge a clamp forward against the groove or ridge of the syringe shield to lock the syringe shield in place when it has been pushed into position. Embodiments are not limited to any particular syringe holder or mount. For example, in some embodiments, the syringe holder may be a device configured to accept and hold a syringe or vial holding the radiopharmaceutical by removably attaching to the syringe or vial body or flanges associated with the syringe or vial. In other embodiments, the syringe holder or mount may be configured to accept and hold a secondary device housing a syringe or vial including a radiopharmaceutical.

Figure 4:
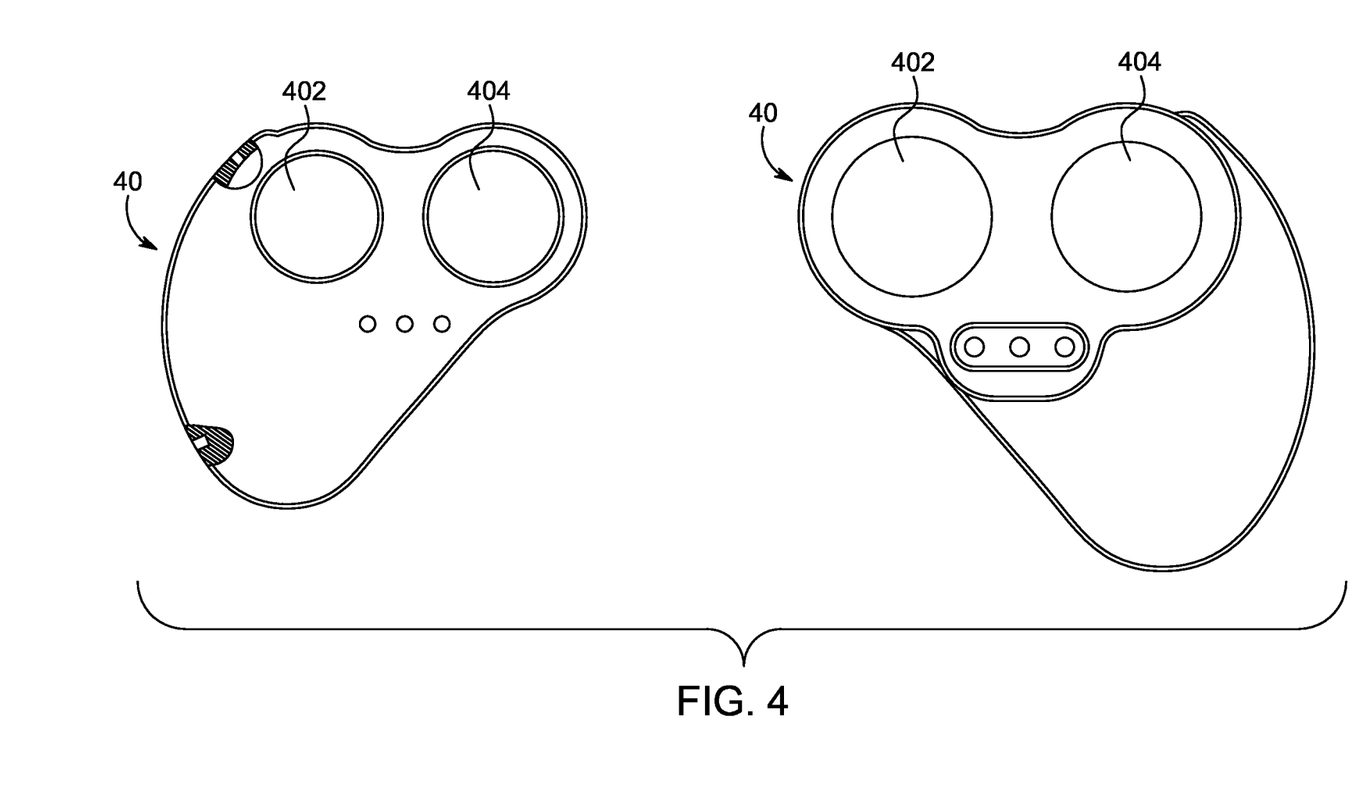
FIG. 4 is a drawing showing a collar syringe shield support.

In certain embodiments, the syringe shield may be attached to a delivery injector body using a collar syringe shield support, and the like or combinations thereof. For example, FIG. 4 is an example of a base plate 40 configured to connect with the syringe shield described above with reference to FIG. 1. Such base plates 40 may be an integral part of a device onto which the syringe shield is designed to interact, or in some embodiments, such base plates 40 may be made as a separate component that can be attached to existing devices as an adapter. Thus, in some embodiments, the base plate 40 may include flanges, holes, clamps, appendages, and the like or other components and combinations thereof for attaching the base plate to the device.

The base plates 40 of such embodiments may generally include one or more orifices 402, 404 positioned to allow actuation devices from the device to contact the syringe or a plunger, stopper, or piston associated with the syringe to expel the contents of the syringe. The base plate 40 may further include a means for attaching the syringe shield to the base plate. For example, in some embodiments, the one or more orifices 402, 404 may include grooves or threads that correspond with grooves or threads on the syringe shield and allow the syringe shield to be screwed into the base plate. In other embodiments, holes may be provided near the orifices 402, 404 that are configured to receive a pin or screw which is received by the orifices in a connector plate (155 and 156 in FIG. 1), and attach the syringe shield to the base plate 40.

Figure 5:
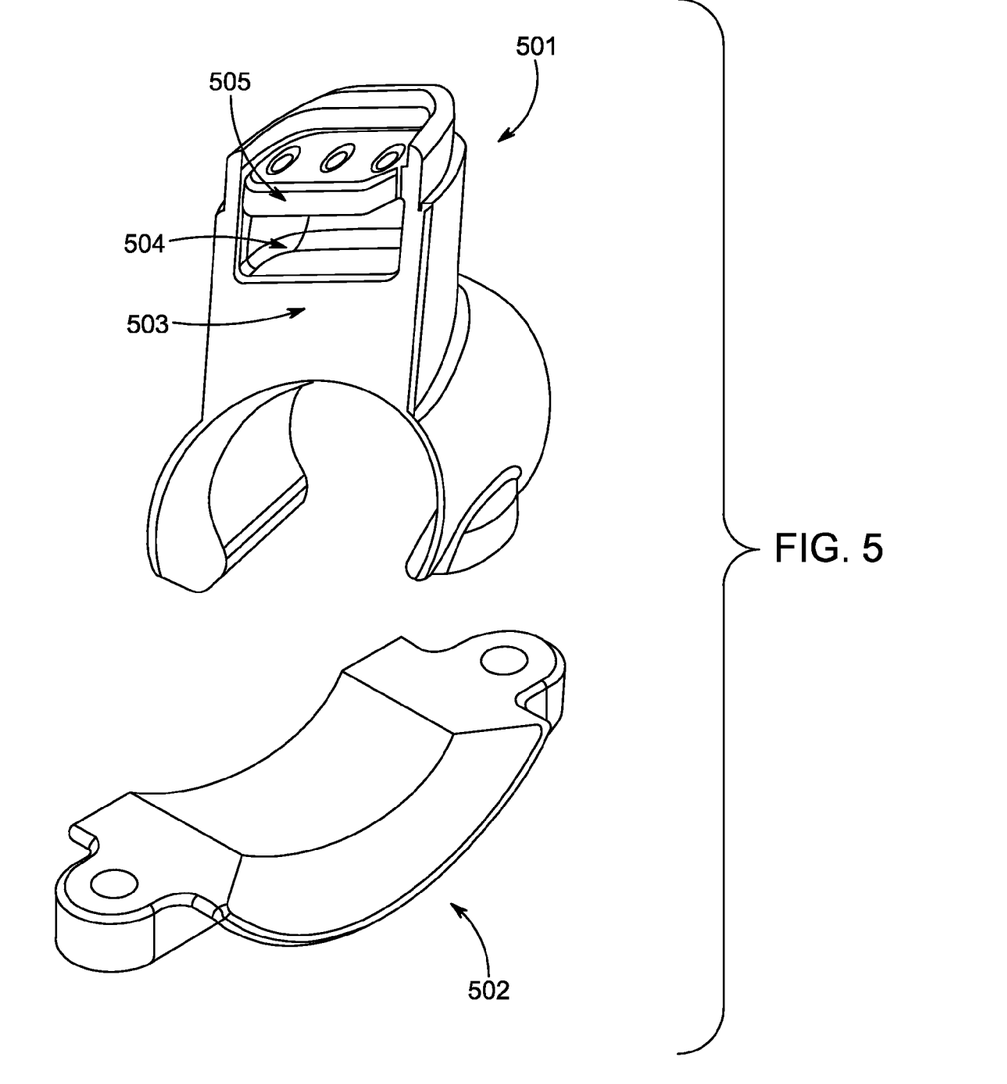
FIG. 5 is a drawing showing a vertical shield support and cap

In some embodiments, the collar syringe shield support is designed to fit over and around the front of a delivery injector body to avoid modification to the injector and to provide free access of the syringes to the injector head for syringe mounting, while providing a relatively immovable base to which to attach the syringe shield. For example, FIG. 5 provides a two piece collar 501, 502 that is designed and configured to encircle a portion of a device, and this collar assembly may be attached to the base plate of the collar syringe shield support by an attachment extension 503. More specifically, the base plate may be received by an opening in the collar mount 501 and used to secure the base plate in place using screws, pins, or another attachment means. The collar mount 501 may include one or more attachment extensions 503 that include a means for attaching the collar to the base plate. As illustrated in FIG. 5, the attachment means includes a groove 504 and a screw-plate 505 that is configured to fit over and connect with an appendage or flange on the base plate. Screws, pins, or another attachment means can be introduced through the screw-plate 505 into corresponding holes or orifices in the appendage or flange on the base plate to connect the collar syringe shield assembly to the base plate. In a particular embodiment, the syringe shield may be permanently or temporarily attached to a Bayer Medrad Spectris Solaris EP injector or similar fluid delivery systems to provide shielding for a drug containing syringe.

In some embodiments, the collar syringe shield assembly may be pivoted on the appendage or flange of the base plate to allow the position of the syringe to change during use without disassembling the collar/syringe shield assembly or removing the collar from the appendage or flange, as shown in FIG. 6. FIG. 6 shows the components of FIG. 4 and FIG. 5 with a syringe shield of FIG. 1 and syringes mounted onto a device. In particular embodiments, the syringe shield can be selectively moved by the operator into a position 601 where the syringe shield is around a syringe, or be moved to a second position 602 for storage on the injector head where it is not surrounding or shielding the syringe. In some embodiments, a locking pin 603 may be provided that fits into holes in the collar syringe shield support, enabling the shield to be locked into position either around a syringe or in a second, storage position not surrounding a syringe. In other embodiments, the locking pin is spring loaded so that it is a part of the syringe shield and not removable such that the pin can be pulled out and spring into the hole when it is moved to the correct position, or the locking pin can be rotated 90 degrees to hold it in the disengaged position to facilitate easier movement between the deployed and stored position and then turned 90 degrees again to engage the hole.

Figure 7:
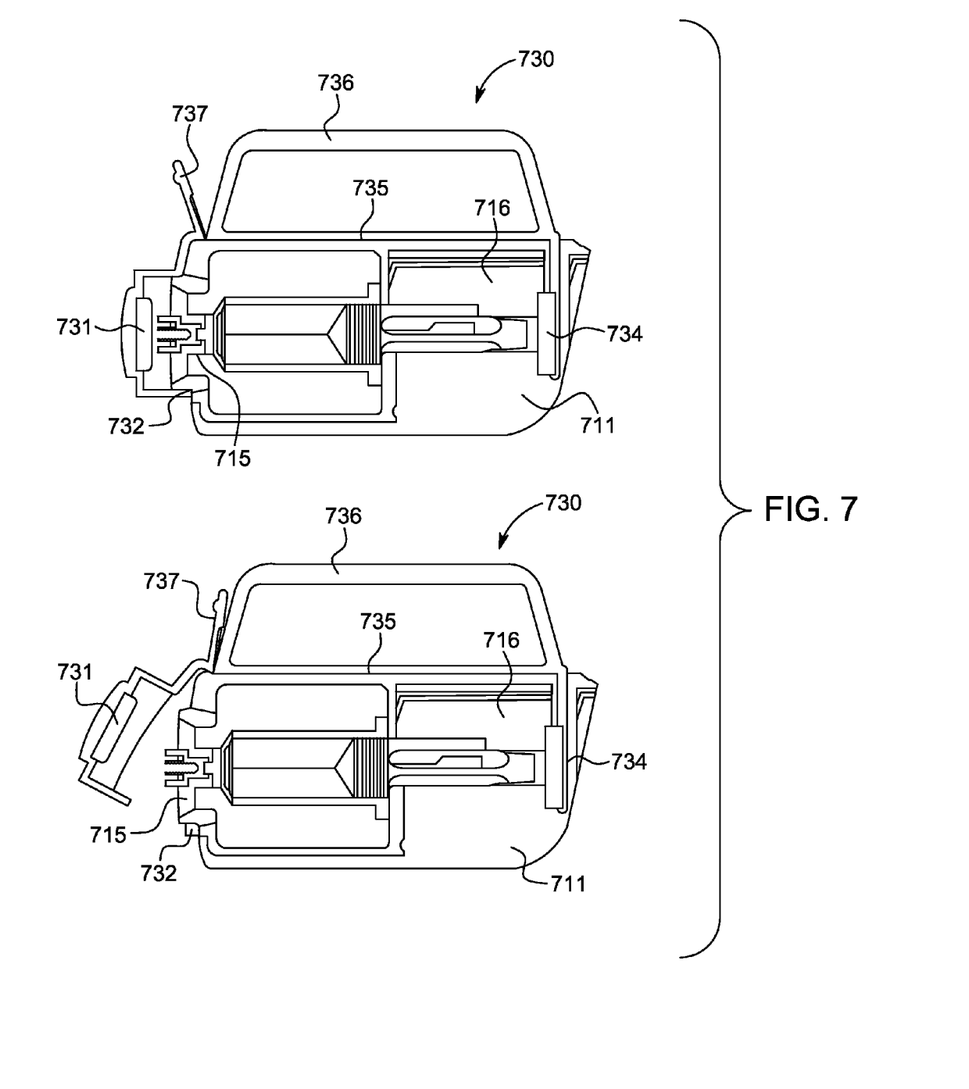
FIG. 7 is a drawing showing a syringe shield and a carrier handle.

Further embodiments include a carrier handle 730 designed to attach to the syringe shield to ease transport of the radiopharmaceutical and reduce exposure to the person carrying the syringe shield. For example, as illustrated in FIG. 7, in some embodiments, a carrier handle 730 may include a tubing bore cover 731 configured and arranged to fit within the tubing bore 715 and/or a groove, flange, 732 or other attachment means associated with the tubing bore. The carrier handle may further include a plunger cover 734 configured and arranged to associate with the enlarged portion of the syringe housing 711 by, for example, contacting the housing within the enlarged portion of the housing 711. In some embodiments, the tubing bore cover 731 and/or the plunger cover 734 may include a material capable of blocking radioactive emissions that is positioned to block emission that could otherwise escape through the tubing bore 715 and the plunger access point 716. In particular embodiments, the carrier handle 730 may include a carrier body 735 that includes a grip portion 736 and the plunger cover 734. The tubing bore cover 731 may be hingedly attached to the carrier body and may include a lever or button 737 that is configured to allow the tubing bore cover to be released from the tubing bore 715 or corresponding flanges and grooves 732 on the housing 711 when the lever or button is depressed.

In operation, the user may grasp the syringe shield 711 by positioning the plunger cover 734 within the plunger access point 716 or within the enlarged portion of the syringe shield 711 while the lever or button 737 is depressed. The tubing bore cover 731 may be positioned over the tubing bore 715 and the lever or button 737 can be released such that the tubing bore cover 731 is properly positioned within the tubing bore 715 and corresponding grooves 732. The carrier handle 730 is thereby sufficiently connected to the syringe shield to allow the user to easily pick up and transport the syringe shield 711 without actually touching the housing itself. To remove the carrier handle 730, the user can position the syringe shield 711 within a delivery injector body to allow the syringe shield 711 to connect to a syringe mount. The lever or button 737 may be depressed releasing the tubing access bore cover 731 from the tubing access bore 715 and corresponding groove 732, and the user may rotate the carrier handle 730 such that the plunger cover 734 is removed from the plunger access point 716 and enlarged portion of the syringe shield 711. Finally, the carrier handle 730 can be withdrawn from the syringe shield 711 while the syringe shield 711 remains mounted on a delivery injector body. Exposure to radioactive emissions from radiopharmaceutical minimalized during transport, and only occurs during loading of the syringe into the syringe shield 711 and installation of the tubing sections after the carrier handle 730 has been removed.

The carrier handle 730 and syringe shield 711 may be made from any material. For example, the carrier handle 730 and syringe shield 711 may be made from a metal, a polymeric material, or combinations thereof. In certain embodiments, the carrier handle 730 may be prepared from a rigid polymeric material such as a polycarbonate that may reduce the weight of the combined syringe shield 711 and the carrier handle 730, while the syringe shield 711 may be prepared from a metal or other material that is capable of blocking radioactive emissions such as tungsten or lead. In still other embodiments, the syringe shield 711 may be made from a metal such as tungsten or lead that is covered in a polymeric material such as a polycarbonate or light weight metal such as aluminum. In still other embodiments, the syringe shield 711 may include a pigment or dye at eliminates exposure of optical tracers to light. For example, in embodiments in which an optical tracer is delivered using the delivery device, the syringe shield 711 may be prepared exclusively from an opaque or colored to absorb particular wavelengths of light to reduce decay of the optical tracer. In such embodiments, the syringe shield 711 may not include a metal or other material to block radioactive emissions, and the radioactive emissions blocking material 712 portion of the devices illustrated may be omitted and replaced with, for example, a polymeric material.

The systems that incorporate the syringe shield of the various embodiments may be configured to deliver any radiopharmaceutical known in the art, and the radiopharmaceutical may be delivered alone or in combination with another pharmaceutical composition. For example, in some embodiments, the system may be designed and configured to deliver $^{47}$Ca—Ca$^{2+}$, $^{11}$C-L-methyl-methionine, $^{14}$C-glycocholic acid $^{14}$C-para-amino benzoic acid (PABA), $^{14}$C-urea, $^{14}$C-d-xylose, $^{51}$Cr-red blood cells, $^{51}$Cr—Cr$^{3+}$, $^{51}$Cr-ethylenediaminetetraacetic acid (EDTA), $^{57}$Co-cyanocobalamin (vitamin B$_{12}$), $^{58}$Co-cyanocobalamin (vitamin B$_{12}$), $^{169}$Er-colloid, $^{18}$F-fluorodeoxyglucose (FDG), $^{18}$F-fluoride, $^{18}$F-fluorocholine, $^{68}$Ga-dotatoc or -dotatate, $^{3}$H-water, $^{111}$In-diethylenetriaminepentaacetic acid (DTPA), $^{111}$In-leukocytes, $^{111}$In-platelets, $^{111}$In-pentetreotide, $^{111}$In-octreotide, $^{123}$I-iodide, $^{123}$I-o-iodohippurate, $^{123}$I-m-iodobenzylguanidine (MIBG), $^{123}$I-FP-CIT, $^{125}$I-fibrinogen, $^{131}$I-iodide, $^{131}$I-m-iodobenzylguanidine (MIBG), $^{59}$Fe—Fe$^{2+}$ or —Fe$^{3+}$, $^{81}$mKr-aqueous, $^{13}$N-ammonia, $^{15}$O-water, $^{32}$P-phosphate $^{82}$Rb-chloride, $^{153}$Sm-ethylenediaminotetramethylenephosphoric acid (EDTMP), $^{75}$Se-selenorcholesterol, $^{75}$Se-23-Seleno-25-homo-tauro-cholate (SeHCAT), $^{22}$Na—Na$^{+}$, $^{24}$Na—Na$^{+}$, $^{89}$Sr-chloride, $^{99m}$Tc-pertechnetate, $^{99m}$Tc-human albumin, $^{99m}$Tc-human albumin macroaggregates or microspheres, $^{99m}$Tc-phosphonates and -phosphate, $^{99m}$Tc-diethylenetriaminepenta-acetic acid (DTPA), $^{99m}$Tc-dimercaptosuccinic acid (V) (DMSA), $^{99m}$Tc-dimercaptosuccinic acid (III) (DMSA), $^{99m}$Tc-colloid, $^{99m}$Tc-hepatic iminodiacetic acid (HIDA), $^{99m}$Tc-denatured red blood cells, $^{99m}$Tc-red blood cells, $^{99m}$Tc-mercaptoacetyltriglycine (MAG3), $^{99m}$Tc-exametazime, $^{99m}$Tc-sestamibi (MIBI-methoxy isobutyl isonitrile), $^{99m}$Tc-sulesomab (IMMU-MN3 murine Fab'-SH antigranulocyte monoclonal antibody fragments), $^{99m}$Tc-human immunoglobulin, $^{99m}$Tc-tetrofosmin, $^{99m}$Tc ethyl cysteinate dimer (ECD), $^{201}$Tl-n+, $^{133}$Xe in isotonic sodium chloride solution, $^{90}$Y-silicate, and the like and combinations thereof. In certain embodiments, the system may be configured for delivery of radiopharmaceuticals for imaging myocardial or other cardiovascular conditions. In such embodiments, the system may be configured to deliver $^{18}$F-fluorodeoxyglucose (FDG), $^{13}$N-ammonia, $^{15}$O-Water, $^{82}$Rb-Chloride, $^{99m}$Tc-pertechnetate, $^{99m}$Tc-human albumin, $^{99m}$Tc-human albumin macroaggregates or microspheres, $^{99m}$Tc-diethylenetriaminepenta-acetic acid (DTPA), $^{99m}$Tc-denatured red blood cells, $^{99m}$Tc-red blood cells, $^{99m}$Tc-exametazime, $^{99m}$Tc-sestamibi (MIBI—methoxy isobutyl isonitrile), $^{99m}$Tc-tetrofosmin, $^{201}$Tl—Tl$^{+}$, and the like and combinations thereof.

Optical tracers used in various embodiments may be derived from any source. For example, in some embodiments, the optical tracer may be a fluorochrome, green fluorescent protein, red fluorescent protein, and luciferin or any other bioluminescent molecule isolated from, for example, ctenophores, coelenterates, mollusca, fish, ostracods, insects, bacteria, crustacea, annelids, and earthworms. In particular embodiments, the optical tracer may be isolated from fireflies, *Mnemiopsis, Beroe ovata, Aequorea, Obelia, Pelagia, Renilla, Pholas Aristostomias, Pachystomias, Poricthys, Cypridina, Aristostomias, Pachystomias, Malacosteus, Gonadostomias, Gaussia, Watensia, Halisturia,* Vampire squid, *Glyphus,* Mycotophids, Vinciguerria, *Howella, Florenciella, Chaudiodus, Melanocostus,* Sea Pens, *Chiroteuthis, Eucleoteuthis, Onychoteuthis, Watasenia,* cuttlefish, *Sepiolina, Oplophorus, Acanthophyra, Sergestes, Gnathophausia, Argyropelecus, Yarella, Diaphus, Gonadostomias, Ptilosarcus,* or *Neoscopelus,* and in certain embodiments, the optical tracer may be luciferin or coelentrazine.

In some embodiments, the system may be configured to administer a single radiopharmaceutical composition, and in other embodiments the system may be configured to deliver two or more different radiopharmaceuticals. In embodiments in which the system is configured to deliver multiple radiopharmaceuticals, the system may allow the operator to switch configurations depending on the intended procedure. The amount of radiopharmaceutical delivered by the system may vary among embodiments and based on the protocol being used. Generally, a doctor, technician, or other qualified personnel can determine an appropriate amount of the radiopharmaceutical to be delivered to a particular subject using metrics regarding the subject known in the art. Because of the flexibility of the system, any amount of radiopharmaceutical can be delivered.

Although various embodiments have been described in detail for the purpose of illustration, it is to be understood that such detail is solely for that purpose and that the disclosure is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment. It is also to be understood that the specific devices and processes illustrated in the attached drawings, and described in the following specification, are simply exemplary embodiments.

We claim:

1. A syringe shield system for a fluid delivery device, the system comprising:
   a collar syringe shield support attached to the fluid delivery device;
   a shield panel having blocking material and a syringe bore configured to correspond to a syringe, wherein the syringe bore has a discharge end aperture and a plunger end aperture; and
   a sleeve encasing the shield panel, wherein the sleeve is coupled to the collar syringe shield support, wherein the sleeve includes a lower sleeve and an upper sleeve having a forward cover and a rearward cover openable independent of the forward cover.

2. The system of claim 1, wherein at least one of the lower sleeve and the upper sleeve is coupled to the collar syringe shield support.

3. The system of claim 1, wherein the sleeve is configured to move between a deployed position and a stored position.

4. The system of claim 1, wherein the sleeve is reversibly coupled to the collar syringe shield support.

5. The system of claim 1, wherein the shield panel includes a bore having a diameter adapted to a shape and a size of a syringe.

6. The system of claim 1, wherein the forward cover is adapted to shield at least a forward end of the sleeve and the rearward cover is adapted to shield at least a rearward end of the sleeve, and wherein at least one of the forward cover and the rearward cover is attached to the sleeve.

7. The system of claim 6, wherein the at least one of the forward cover and the rearward cover is removably attached to the sleeve.

8. The system of claim 6, wherein the forward cover has a bore configured to correspond to a discharge end of the syringe.

9. The system of claim 1, wherein the collar syringe shield support includes a collar mount configured to attach to the fluid delivery device.

10. The system of claim 1, wherein the collar syringe shield support is removably attachable to the fluid delivery device as an adapter.

11. The system of claim 1, wherein the collar syringe shield support includes at least one orifice wherein an actuation device of the fluid delivery device can pass through the at least one orifice to contact the syringe.

12. The system of claim 1, wherein the shield panel is integral to the sleeve.

13. The system of claim 1, wherein the discharge end aperture of the syringe bore is smaller in diameter than the plunger end aperture of the syringe bore, wherein the discharge end aperture is designed to correspond to a discharge end of the syringe.

14. The system of claim 1, wherein the blocking material is selected from the group consisting of radioactive emission blocking material, optical blocking material, and any combination thereof.

15. A syringe shield system for a fluid delivery device, the system comprising:
    a syringe mount configured to attach to the fluid delivery device;
    a shield panel including at least a blocking material and having a syringe bore configured to correspond to a syringe, wherein the syringe bore has a discharge end aperture and a plunger end aperture; and
    a sleeve encasing the shield panel and having a sleeve attachment coupled to the syringe mount, wherein the sleeve includes a lower sleeve and an upper sleeve having a forward cover and a rearward cover openable independent of the forward cover.

16. The system of claim 15, wherein the sleeve attachment is coupled to at least one of the lower sleeve and the upper sleeve.

17. The system of claim 15, wherein one of the lower sleeve and the upper sleeve is removably attachable to the other of the lower sleeve and the upper sleeve.

18. The system of claim 15, wherein the sleeve attachment is one of a flange and a groove.

19. The system of claim 15, wherein the shield panel includes a plurality of sections.

20. The system of claim 15, wherein the forward cover of the sleeve is attached to a discharge end of the shield panel, the forward cover including a blocking material and having a longitudinal axis bore configured to receive a discharge end of the syringe.

* * * * *

UNITED STATES PATENT AND TRADEMARK OFFICE
CERTIFICATE OF CORRECTION

PATENT NO. : 9,707,342 B2
APPLICATION NO. : 14/844355
DATED : July 18, 2017
INVENTOR(S) : Uber, III et al.

It is certified that error appears in the above-identified patent and that said Letters Patent is hereby corrected as shown below:

In the Specification

In Column 11, Lines 65-66, delete "$^{14}$C-glycocholic acid" and insert -- $^{14}$C-glycocholic acid, --, therefor.

In Column 12, Line 11, delete "$^{32}$P-phosphate" and insert -- $^{32}$P-phosphate, --, therefor.

In Column 12, Line 50, delete "Poricthys," and insert -- Porichthys, --, therefor.

In Column 12, Line 52, delete "Mycotophids," and insert -- Myctophids, --, therefor.

In Column 12, Lines 56-57, delete "Diaphus, Gonadostomias," and insert -- Diaphus, --, therefor.

In Column 12, Line 58, delete "coelentrazine." and insert -- coelenterazine. --, therefor.

Signed and Sealed this
Sixteenth Day of January, 2018

Joseph Matal
*Performing the Functions and Duties of the
Under Secretary of Commerce for Intellectual Property and
Director of the United States Patent and Trademark Office*